Oct. 4, 1966 W. FLEMER, JR Plant Pat. 2,675
GINKGO TREE
Filed Sept. 28, 1965
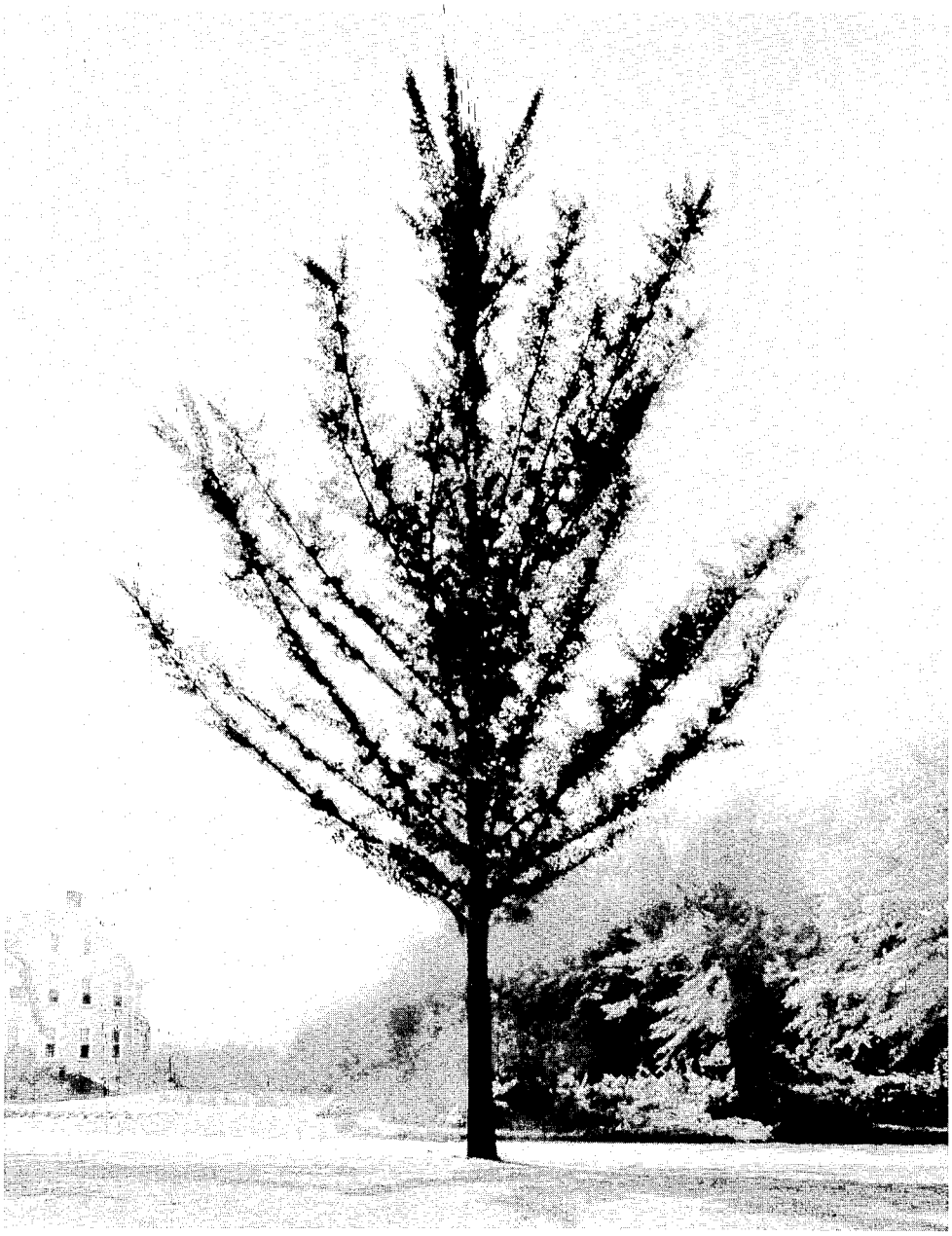
Inventor.
William Flemer, Jr.
By: Robb & Robb
Attorneys.

United States Patent Office

Plant Pat. 2,675
Patented Oct. 4, 1966

2,675
GINKGO TREE

William Flemer, Jr., Princeton, N.J., assignor to Princeton Nurserymen's Research Associates, Princeton, N.J., a partnership

Filed Sept. 28, 1965, Ser. No. 491,051
1 Claim. (Cl. Plt.—51)

The present invention relates to a new and distinct variety of ginkgo tree of the *Ginkgo biloba* type, which was originated by me as a seedling of the variety botanically known as *Ginkgo biloba* (unpatented).

As the result of this origination, I have produced a new and improved variety of ginkgo tree which is distinguished from its parent, as well as from all other varieties known to me, as evidenced by the following unique combination of characteristics which are outstanding therein:

(1) Perfect regularity of branching habit unlike the sparse and asymmetrical branching which is characteristic of normal ginkgo seedlings;

(2) A strong central leader or trunk which does not require staking to induce straightness as required by the spreading habit of other grafted male ginkgo clones;

(3) A uniform and clear gold autumn foliage color which is typical of other regular ginkgo varieties and which therefore is not new or distinctive in itself;

(4) Ease of propagation either by grafting onto seedling understocks or by soft wood cuttings; and (5) Absence of ill-smelling fruit as the consequence of its male sex.

Asexual reproduction of my new variety by both grafting and vegetative cuttings, as performed in South Brunswick Township, New Jersey, shows that the foregoing characteristics and distinctions come true and are established and transmitted through succeeding propagations.

The accompanying drawing shows a typical specimen tree of my new variety of ginkgo tree which illustrates its characteristic habits of growth.

The following is a detailed description of my new variety, with color terminology in accordance with the Nickerson Color Fan, published by Munsell Color Company, Inc., of Baltimore, Maryland, except where general color terms of ordinary dictionary significance are obvious, as based on specimens grown in South Brunswick Township, New Jersey:

Parentage: Seedling of *Ginkgo biloba.*

Propagation: Holds its distinguishing characteristics through succeeding propagations by both grafting and cuttings.

Tree: Large; tall (about 55 feet); about 40 feet wide; upright and spreading; hardy.

*Trunk.*—Stocky; rough.

*Branches.*—Straight; stocky; rough when mature; borne in a regular spreading pattern.

*Head or crown.*—Regular; excurrent branching habit, with branches evenly spaced around a central leader.

*Lenticels.*—Few; large.

Foliage:

*Leaves.*—Abundant; very thick; leathery. Length (including petiole)—from 10 to 11 cm. Width—from 9 to 10 cm. Shape—fan-shaped; incised into 2 equal lobes, with depth of sinus approximately half of depth of blade and ranging from about 2½ cm. to 3 cm. deep. Color—moderate Olive Green, Plate 5GY 4/3. Margin—sinuate. Petiole—long (from about 4 cm. to 6 cm.). Glands—none. Stipules—none.

Flower buds: Hardy; hemispherical. Color—pale brown.

Flowers: Long staminate catkin; not ornamental.

*Quantity.*—Normal.

*Size.*—Medium. Length—from about 3 cm. to 3½ cm. Width—about 1 cm.

Fruit: None, due to male sex, and therefore completely free from the usual ill-smelling fruit usually borne by female ginkgo trees.

I claim:

A new and distinct variety of ginkgo tree, substantially as herein shown and described, characterized particularly as to novelty by the unique combination of perfect regularity of branching habit, a strong central leader or trunk which does not require staking to induce straightness, a uniform and clear gold autumn foliage color, ease of propagation by both grafting and cuttings, and a complete freedom from the production of ill-smelling fruit.

No references cited.

ABRAHAM G. STONE, *Primary Examiner.*

R. E. BAGWILL, *Assistant Examiner.*